US008313442B2

(12) United States Patent
Kassem

(10) Patent No.: US 8,313,442 B2
(45) Date of Patent: Nov. 20, 2012

(54) CEREBRAL COMPLIANCE MONITORING

(75) Inventor: Salim Kassem, North Attleboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 36 days.

(21) Appl. No.: 12/625,627

(22) Filed: Nov. 25, 2009

(65) Prior Publication Data

US 2011/0092846 A1   Apr. 21, 2011

Related U.S. Application Data

(60) Provisional application No. 61/253,623, filed on Oct. 21, 2009.

(51) Int. Cl.
*A61B 5/00* (2006.01)
(52) U.S. Cl. ....................................................... 600/561
(58) Field of Classification Search ................. 600/378, 600/561, 544, 545, 552
See application file for complete search history.

(56) References Cited

U.S. PATENT DOCUMENTS

| | | | |
|---|---|---|---|
| 4,062,354 A | 12/1977 | Taylor | |
| 4,080,653 A | 3/1978 | Barnes, Jr. | |
| 4,312,361 A | 1/1982 | Nicholson | |
| 4,519,401 A | 5/1985 | Ko | |
| 4,893,630 A * | 1/1990 | Bray, Jr. | 600/484 |
| 5,108,364 A | 4/1992 | Takezawa | |
| 5,117,835 A * | 6/1992 | Mick | 600/561 |
| 5,117,836 A | 6/1992 | Millar | |
| 5,325,865 A | 7/1994 | Beckman | |
| 5,579,774 A | 12/1996 | Miller | |
| 5,997,484 A * | 12/1999 | Sugahara | 600/561 |
| 6,171,242 B1 * | 1/2001 | Amano et al. | 600/423 |
| 6,413,227 B1 * | 7/2002 | Yost et al. | 600/561 |
| 6,537,232 B1 | 3/2003 | Kucharczyk | |
| 6,950,699 B1 | 9/2005 | Manwaring | |
| 7,198,602 B2 | 4/2007 | Eide | |
| 7,335,162 B2 | 2/2008 | Eide | |
| 7,559,898 B2 | 7/2009 | Eide | |

(Continued)

FOREIGN PATENT DOCUMENTS

DE    19637141 A1    3/1998

(Continued)

OTHER PUBLICATIONS

Brean, A. et al.; Comparison of Intracranial Pressure Measured Simultaneously Within the Brain Parenchyma and Cerebral Ventricles; Journal of Clinical Monitoring and Computing (2006) 20:411-414; Springer 2006.

(Continued)

*Primary Examiner* — Max Hindenburg
*Assistant Examiner* — Charles Becker

(57) ABSTRACT

A system and method for monitoring cerebral compliance of a patient by placing a first pressure sensor in a first sub-dural location, preferably a sub-meningeal location, within the brain of the patient and placing at least a second pressure sensor in a second sub-dural location, preferably a sub-meningeal location, within the brain which is different from the first location. At least one parameter from each of the signals derived from the pressure sensors is compared to estimate cerebral compliance for the patient. Alternatively, at least a single pressure sensor is utilized with a generator of reference signals having at least two different frequencies. Preferably, any change in cerebral compliance is detected by determining a change in the compared parameter, and a perceptible indication is generated when cerebral compliance deviates beyond a pre-selected value.

23 Claims, 4 Drawing Sheets

U.S. PATENT DOCUMENTS

| | | | |
|---|---|---|---|
| 2005/0203438 | A1 | 9/2005 | Manwaring |
| 2007/0060835 | A1 | 3/2007 | Eide |
| 2007/0161891 | A1 | 7/2007 | Moore |
| 2008/0139959 | A1* | 6/2008 | Miethke et al. ............... 600/561 |
| 2009/0069711 | A1 | 3/2009 | Eide |
| 2009/0143654 | A1 | 6/2009 | Funane |
| 2009/0143656 | A1 | 6/2009 | Manwaring |
| 2009/0177279 | A1* | 7/2009 | Luciano et al. ............ 623/11.11 |

FOREIGN PATENT DOCUMENTS

DE   20116879 U1   12/2001

OTHER PUBLICATIONS

Kolsen-Petersen, J. A. et al; Monitoring of Intracranial Pressure (ICP): A Review; Monitoring of Cerebral and Spinal Haemodynamics During Neurosurgery; 2008; pp. 1-58; ISBN 978-3-540-77872-1 (Print) 978-3-540-77873-8 (Online); Springer Berlin Heidelberg.

Pillai, S. et al.; Cerebral perfusion pressure management of severe diffuse head injury: Effect on brain compliance and intracranial pressure; Neurology India Mar. 2004 pp. 67-71 vol. 52 Issue 1; www.neurologyindia.com; India.

Portella, G. et al.; Continuous cerebral compliance monitoring in severe head injury: its relationship with intracranial pressure and cerebral perfusion pressure; Acta Neurochir (Wien) (2005) 147: 707-713; Springer-Verlag 2005; Austria.

Seder, D.B. et al; Multimodality Monitoring in Patients with Elevated Intracranial Pressure; Intensive Care Medicine; 2008; pp. 811-821; ISBN 978-0-387-77382-7 (Print) 978-0-387-77383-4 (Online); Springer New York.

Steiner, L.A. et al.; Monitoring the injured brain: ICP and CBF; British Journal of Anaesthesia 97 (1): 26-38 (2006).

European Search Report for Appln. No. 10251830.5 dated May 24, 2011.

* cited by examiner

CEREBRAL COMPLIANCE MONITORING

BACKGROUND OF THE INVENTION

1. Field of the Invention

The invention relates to a system and method for monitoring cerebral compliance in a patient and more particularly to comparing repeatedly, preferably continuously, signals from at least two pressure sensors placed at different sub-dural locations, preferably sub-meningeal locations, within the brain of the patient to detect changes in cerebral compliance. Alternatively, two or more generated reference frequencies are measured at one or more pressure sensor locations.

2. Description of the Related Art

Human brain tissue includes gray and white matter suspended in cerebrospinal fluid within the cranium and nourished by blood delivered through cerebral arteries. The gray matter has closely spaced cell bodies of neurons, such as in the cerebral cortex, and the underlying white matter contains densely packed axons that transmit signals to other neurons. Brain tissue has different densities and comprises approximately eighty percent of the intracranial content, with blood and cerebrospinal fluid each normally comprising approximately ten percent.

Cerebrospinal fluid is produced in several connected chambers known as ventricles and typically is renewed four to five times per day. Cerebrospinal fluid in a healthy human flows slowly and continuously through the ventricles, propelled by pulsations of the cerebral arteries, flows around the brain tissues and the spinal column, and then through small openings into the arachnoid membrane, which is the middle layer of the meninges surrounding the brain parenchyma and ventricles, where the fluid is finally reabsorbed into the bloodstream.

Under normal conditions, bodily mechanisms compensate for a change in fluid volume within the cranium through tissue resilience and by adjusting the total volume of blood and cerebrospinal fluid so that a small increase in fluid volume does not increase intracranial pressure. Similarly, a healthy brain compensates for an increase in intracranial pressure to minimize a corresponding increase in intracranial volume. This volume- and pressure-relationship can be explained in terms of cerebral compliance, which term is intended to include herein the terms elastance and intracranial compliance.

The brain is compliant as long as a person's auto-regulatory mechanism can compensate for any change in volume. As soon as the brain's auto-regulation or compensatory mechanisms fail, blood and cerebrospinal fluid cannot be displaced, and the brain can no longer adapt to any increase in fluid volume.

A reduction in cerebral compliance eventually will lead to an undesired increase in intracranial pressure, such as described by Seder et al. in "Multimodality Monitoring in Patients with Elevated Intracranial Pressure" from the book "Intensive Care Medicine" published by Springer New York (2008). Reduced cerebral compliance is also referred to as increased brain stiffness or as stiff brain. As more fluid volume is added, a threshold is reached beyond which small increases in volume lead to dramatic and unhealthy increases in intracranial pressure.

Intracranial pressure has been measured at a number of epi-dural and sub-dural locations, such as described by Steiner et al. in "Monitoring the injured brain: ICP and CBF", British Journal of Anaesthesia 97(1): 26-38 (2006) and by Brean et al. in "Comparison of Intracranial Pressure Measured Simultaneously Within the Brain Parenchyma and Cerebral Ventricles", Journal of Clinical Monitoring and Computing 20: 411-414 (2006).

In an early method of determining cerebral compliance, one or more volumes of fluid were added intracranially to produce intracranial pressure variations that were studied by directly measuring intracranial pressure. Cerebral compliance has been estimated over the years by various techniques including studying cerebral perfusion pressure, which has been calculated by measuring intracranial pressure and then subtracting it from systemic blood pressure or mean arterial pressure to obtain a cerebral perfusion pressure value such as described by Portella et al. in "Continuous cerebral compliance monitoring in severe head injury: its relationship with intracranial pressure and cerebral perfusion pressure", Acta Neurochirurgica (Wein) (2005) 147: 707-713. In some procedures, a ventricular catheter has been placed in a brain ventricle to continuously monitor intracranial pressure while an indwelling radial artery catheter with pressure transducer measures mean arterial pressure.

The Spiegelberg system uses a double lumen ventricular catheter having an air pouch mounted at its tip. Cerebral compliance is calculated from a moving average of small increases in intracranial pressure caused by up to several hundred pulses of pouch-added volume. A stable average is developed and then mean cerebral compliance is measured minute-by-minute, which is also described in the above-referenced Portella et al. article. However, this technique can have a poor frequency response, that is, one or more minutes may pass while the Spiegelberg system only posts a single mean value.

In U.S. Publication No. 2009/0143656, Manwaring et al. describe certain systems and methods of measuring intracranial pressure and determining cerebral compliance by detecting phase shifts in pulsatile perfusion flow signals derived from a first noninvasive intracranial flow sensor, such as an oximeter positioned on the forehead next to a supraorbital artery or a tympanic membrane displacement sensor positioned in the ear canal, and a second noninvasive extracranial sensor.

Several techniques for obtaining and processing pressure-related signals are described by Eide in U.S. Pat. Nos. 7,335,162 and 7,559,898 and U.S. Publication No. 2009/0069711 using one or two intracranial pressure sensors, either alone or with an epi-dural or extracranial sensor.

Kucharczyk et al. in U.S. Pat. No. 6,537,232 disclose a device and method for monitoring intracranial pressure during magnetic resonance image-guided procedures such as intracranial drug delivery. One or more pressure sensors are positioned along a catheter to deliver feedback as fluids are injected or withdrawn. Multiple pressure sensors are utilized to detect and measure pressure gradients during drug delivery.

It is therefore desirable to have a simpler, more rapid and more accurate technique for monitoring cerebral compliance.

SUMMARY OF THE INVENTION

An object of the present invention is to provide substantially continuous and accurate monitoring of cerebral compliance in a patient.

Another object of the present invention is to rapidly estimate cerebral compliance and detect changes therein.

A further object of the invention is to monitor cerebral compliance without injecting gas or liquid into the cranium of the patient, that is, without artificially inducing volume changes within the cranium.

This invention results from the realization that comparison of pressures measured at different sub-dural locations, preferably sub-meningeal locations, or comparison of two or more frequency measurements at one or more pressure sensor locations, can be utilized to rapidly monitor and detect changes in cerebral compliance. The term sub-dural as used herein is intended to include all tissues, fluids and spaces underlying the outermost layer of the dura mater of the meninges, and therefore includes intra-dural sinuses such as the superior sagittal sinus, as well as gray matter, white matter and the ventricles. The term sub-meningeal as used herein is intended to include everything underlying the pia mater, which is the inner-most layer of the meninges; in other words, the term sub-meningeal excludes the arachnoid and dura mater membranes and any spaces or sinuses within them. The term brain parenchyma as used herein is intended to include gray matter, white matter and other essential parts of the brain providing its function.

This invention features a system and method by which cerebral compliance within brain of a patient is monitored using at least first and second pressure sensors, or by using at least two generated reference frequencies with at least one pressure sensor. The first pressure sensor is placed in a first sub-dural location, and the second pressure sensor is placed in a second sub-dural location which is different from the first location. At least one parameter from each of the signals derived from the pressure sensors is compared to estimate cerebral compliance for the patient.

In a preferred embodiment, the comparing includes determining at least one of a phase difference, a change in slope, and an amplitude difference between the signals. The first location of a pressure sensor is within a ventricle of the brain and the second location is within a tissue of the brain parenchyma. Alternatively, the first and second locations are in different tissues within the brain parenchyma, such as the first location being within white matter of the brain and the second location being within gray matter of the brain. In one embodiment, the first and second locations are within different hemispheres of the brain.

In some embodiments, the first and second sensors are provided on separate structures, such as portions of catheters, shunts or probes, that are independently positionable in different sub-dural, preferably sub-meningeal locations. In one embodiment, a single access burr hole through the cranium is created and the structures are inserted through the burr hole into the first and second locations. In other embodiments, at least a third pressure sensor is provided and positioned in a tissue that is different than tissue at the first and second locations.

In a further embodiment, an initial difference is established between the signals derived from the pressure sensors, and a change in the difference between the signals is detected to determine a change in cerebral compliance. A perceptible indication is generated when cerebral compliance deviates beyond a preselected value. In one embodiment, a visual or auditory indication, such as an alarm symbol or sound, warns when cerebral compliance drops below a preselected level. In another embodiment, at least one internal or external reference signal, such as a finite pressure propagating wave, is generated to travel within the brain without changing the volume within the cranium, and the parameter from each of the derived signals is compared with the reference signal.

When at least two reference frequencies are utilized, at least a first pressure sensor is connected to a system which generates at least first and second reference pressure propagating signals that travel within the brain, the first reference signal having a first frequency and the second reference signal having a second frequency which differs from that of the first frequency. The system compares at least one parameter relating to the first and second reference signals from signals derived from the pressure sensor to estimate cerebral compliance for the patient.

This invention may also be expressed as a system and method for monitoring cerebral compliance below the dura mater of the meninges surrounding the brain of a patient by using at least first and second pressure sensors, placing the first pressure sensor in a first sub-dural, preferably sub-meningeal location to generate a first waveform, and placing the second pressure sensor in a second location within the brain parenchyma which is different from the first location to generate a second waveform. The system and method further include comparing at least one of phase, slope, amplitude or other derived waveform feature of each of the waveforms obtained from the pressure sensors to estimate cerebral compliance for the patient.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

Figure 1A:
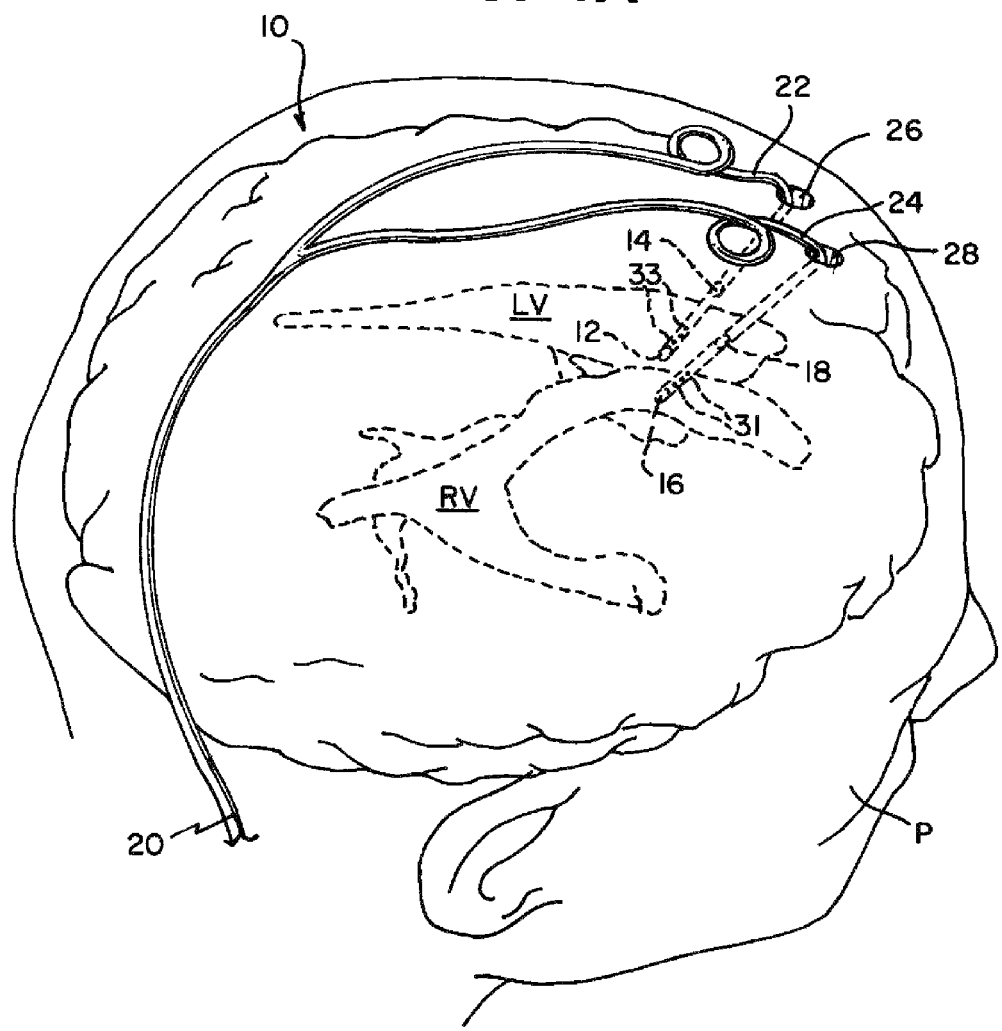
FIG. 1A is a cross-sectional perspective view of a patient showing pressure sensors positioned at different sub-dural locations within the brain according to one embodiment of the present invention.

FIG. 1A illustrates a portion of system 10 according to the present invention having pressure sensors 12 and 14 carried by left branch 22 of catheter 20 and having pressure sensors 16 and 18 carried by right branch 24 of catheter 20 placed below the outermost layer of the dura mater of the meninges surrounding the brain of a patient P. In this construction, left catheter branch 22 passes into the cranium through access burr hole 26 above the left hemisphere and right branch 24 passes through access burr hole 28 above the right hemisphere. Pressure sensor 12 is positioned within left ventricle LV and sensor 16 is positioned in right ventricle RV. Pressure sensors 14 and 18 are positioned in different tissue of the brain parenchyma as described in more detail below.

Figure 1B:
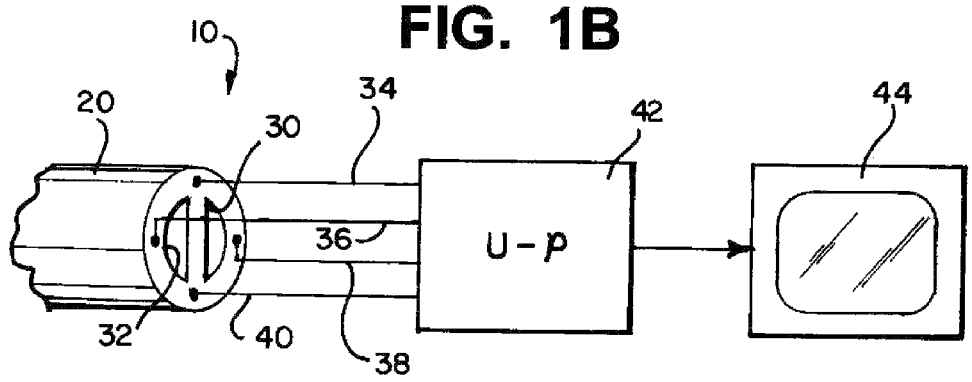
FIG. 1B is a schematic diagram of the signal processing portion of a system according to the present invention.

FIG. 1B shows another portion of catheter 20 having dual lumens 30 and 32 which are in fluid communication with ventricles LV and RV, FIG. 1A, through inlet holes 31 and 33 near pressure sensors 16 and 12, respectively. Catheter 20 carries four electrical leads 34, 36, 38 and 40, each of which comprises one or more wires and transmits a signal from pressure sensors 16, 18, 12 and 14, respectively, to signal processor 42. One or more parameters of signals derived from pressure sensors 12, 14, 16 and/or 18 are time-indexed and compared as described in more detail below to monitor cerebral compliance according to the present invention. Visual and/or audio indicia of the comparison is presented on display 44 to inform an operator of system 10 whether cerebral compliance of the patient remains within preselected levels or whether a change in cerebral compliance has been detected by system 10.

In the construction illustrated in FIGS. 1A and 1B, the tips of catheter branches 22 and 24 are placed such that inlet holes 31 and 33 communicate with cerebrospinal fluid in ventricles RV and LV, respectively. Accordingly, pressure sensors 16 and 12 are disposed in ventricles RV and LV. Because some embodiments of the present invention only require two pressure sensors, one or two of the pressure sensors 12, 14, 16 or 18 could be omitted or disconnected if more simplified signal processing is desired.

Figure 2:
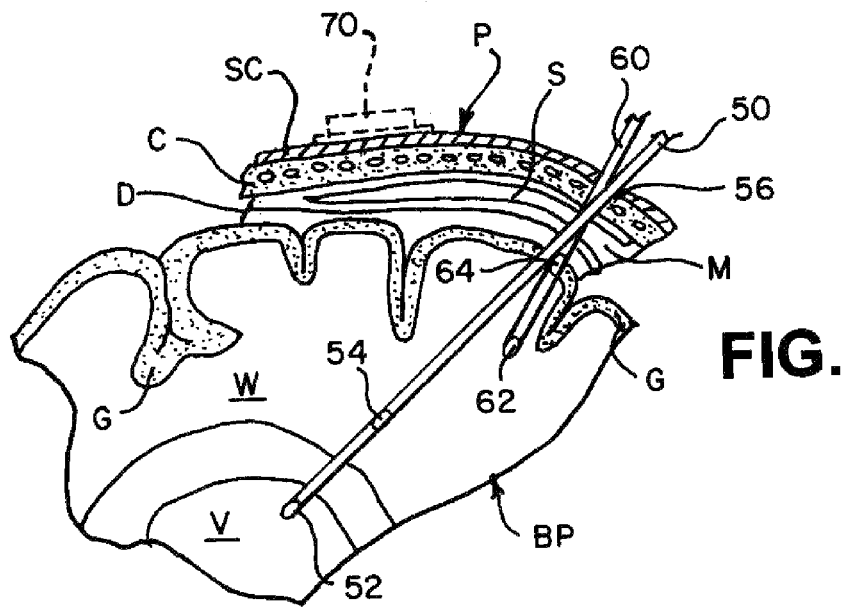
FIG. 2 is a partial side cross-sectional view of two separate probes each carrying two pressure sensors which are positioned below the meninges surrounding the brain according to another embodiment of the present invention.

Positioning two or more pressure sensors according to the present invention is illustrated in FIG. 2. Probe 50 carries first pressure sensor 52 and second pressure sensor 54 and is placed into burr hole 56 in cranium C underlying scalp SC of patient P. Probe 50 is passed through dura mater D of meninges M, which defines sinus S, then gray matter G and white matter W of brain parenchyma BP to position sensor 52 in ventricle V. Preferably, sensor 54 is spaced more than two centimetres from sensor 52, more preferably approximately three centimetres or greater, so that sensor 54 is clearly placed within white matter W. In another construction, a separate probe 60 carrying pressure sensors 62 and 64 is also inserted through bore 56 to place sensor 62 in white matter W and to place sensor 64 in gray matter G or in another sub-dural, preferably sub-meningeal location. In yet another construction, probes 50 and 60 each carry only a single pressure sensor, such as CODMAN MicroSensor pressure sensing probes currently commercially available with ICP EXPRESS Monitor from Codman & Shurtleff, Inc. of Raynham, Mass. Other types of pressure sensors can be utilized according to the present invention. For all of the above-mentioned constructions, it is preferable that at least two pressure sensors, carried by one or more supporting structures such as probes, shunts or catheters, are placed in locations within the brain parenchyma and/or ventricles that have different densities or tissue qualities. Alternatively, at least two pressure sensors are placed in different hemispheres such as shown in FIG. 1A, or at least one pressure sensor is utilized with multiple reference signals as described in more detail below.

Figure 3A:
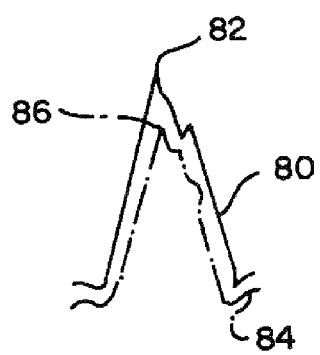
FIG. 3A depicts at least one pressure signal having a lower amplitude relative to a first signal.
Figure 3B:
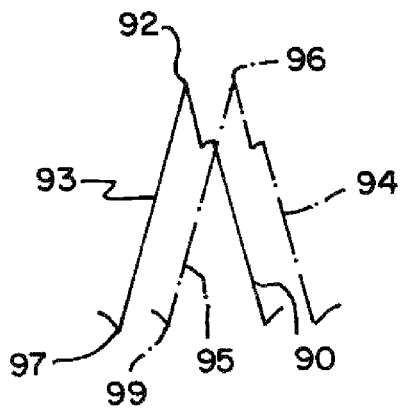
FIG. 3B illustrates at least one pressure signal having a phase shift relative to a first signal.

Examples of signals derivable from the two or more pressure sensors placed according to the present invention, for which one or more parameters are compared, are depicted in FIGS. 3A and 3B. First signal 80 having peak 82 is compared to second signal 84 having a lower amplitude or waveform as shown by second, lower peak 86.

In FIG. 3B, first signal 90 having peak 92 is compared to second, phase-shifted signal 94 having a second, delayed peak 96. In yet other embodiments, the difference in timing of first derivative positions 93 and 95, having the greatest changes of rising slope of waveforms 90 and 94, are utilized by themselves or are used to assist location and comparison of take-off points 97, 99, respectively.

Figure 4A:
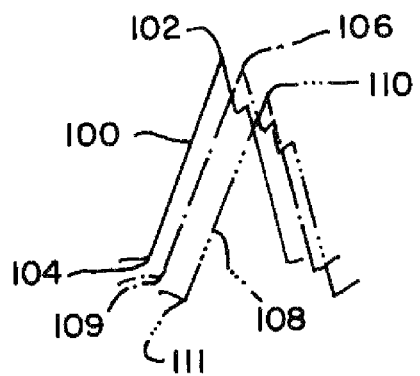
FIG. 4A illustrates multiple pressure signals having both phase and amplitude differences relative to a first signal.

A more compliant brain typically generates signals with increased phase shifts, shallower slopes and decreased amplitudes as illustrated in FIG. 4A by second and third waveforms 104 and 108 relative to first waveform 100 having peak 102. Second and third peaks 106, 110 are both lower and time-delayed relative to first peak 102, as well as having lower, delayed take-off points 109, 111. In one cerebral compliance condition, third waveform 108 is derived from first sensor 52, FIG. 2, and the second waveform 104 represents signals derived from sensors 54 and 62 which are both located in white matter W. The first waveform 100 is derived from sensor 64 positioned in gray matter G, which has approximately twice the concentration of blood vessels because its metabolic needs are higher than for white matter W, and therefore is expected to react faster to cardiac and/or respiratory pulsatility. Using an array of three or more pressure sensors enables creation of an improved map or indicator of cerebral compliance in different brain tissues and/or hemispheres. In a compliant brain, the arterioles, capillaries and ventricles are pliant enough to absorb or attenuate at least some of the pressure pulsatility.

In a low-compliance, stiff-brain condition, all four waveforms appear to be substantially the same. In other words, the pressure created by an inrush of blood from the cardiac cycle or other pressure pulse source cannot be auto-regulated and the increase in pressure is detectable almost immediately throughout the entire brain.

In one construction, one or more parameter values such as certain minimum phase shifts, slopes including take-off points, frequency components, and/or amplitude decreases are preselected as thresholds. When the difference in those parameters approaches the preselected values, a visual and/or audio warning is generated to indicate that cerebral compliance is low. In another construction, a baseline is established for pressure sensors placed within the brain parenchyma and a warning is generated when one or more signal parameters deviate from the baseline.

Figure 4B:
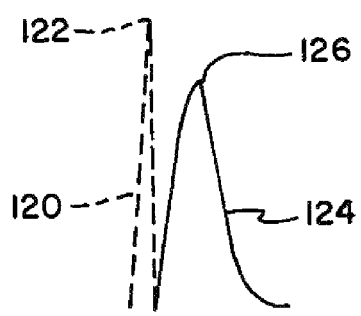
FIG. 4B illustrates at least one pressure signal relative to an externally generated reference pressure wave to estimate cerebral compliance according to another embodiment of the present invention.

FIG. 4B illustrates a reference pressure propagating signal 120 produced by an energy source 70, shown in phantom in FIG. 2. In one construction, energy source 70 includes a pressure transducer external to the cranium to produce a sonic pressure pulse having one or more frequencies and/or waveforms that are different from cardiac or respiratory pulsatility. Two or more pressure sensors placed at different locations according to the present invention are utilized to detect differences in the manner in which the reference signal travels through those locations. In another construction, energy source 70 is connected to a transducer positioned within the cranium, either epi-dural or sub-dural, to internally generate the reference signal 120, FIG. 4B.

The introduction of a known pressure waveform into the brain parenchyma can enhance signal analysis in several ways. First, the timing and duration of the reference signal 120, including that of reference peak 122, is known and can be readily compared to the time-index of signals 124 received by the pressure sensors. Second, filters can be selected to reduce non-target frequencies or waveforms. Third, a higher amplitude and frequency component will improve signal-to-noise ratio. For example, the timing and magnitude of detected peak 126 can be readily compared to known reference peak 122.

When at least two reference frequencies are utilized according to another construction of the present invention, at least a first pressure sensor is connected to a system which generates at least first and second reference pressure propagating signals, such as from energy source 70, FIG. 2, that travel within the brain, the first reference signal having a first frequency and the second reference signal having a second frequency which differs from that of the first frequency. The system compares at least one parameter relating to the first and second reference signals from signals derived from the pressure sensor to estimate cerebral compliance for the patient. In other words, the frequency content of the measured signal is expected to vary according to the compliance state of the brain tissue. A compliant brain will filter out some of the higher frequencies while those same frequencies will become measurable in a stiff brain.

Figure 5:
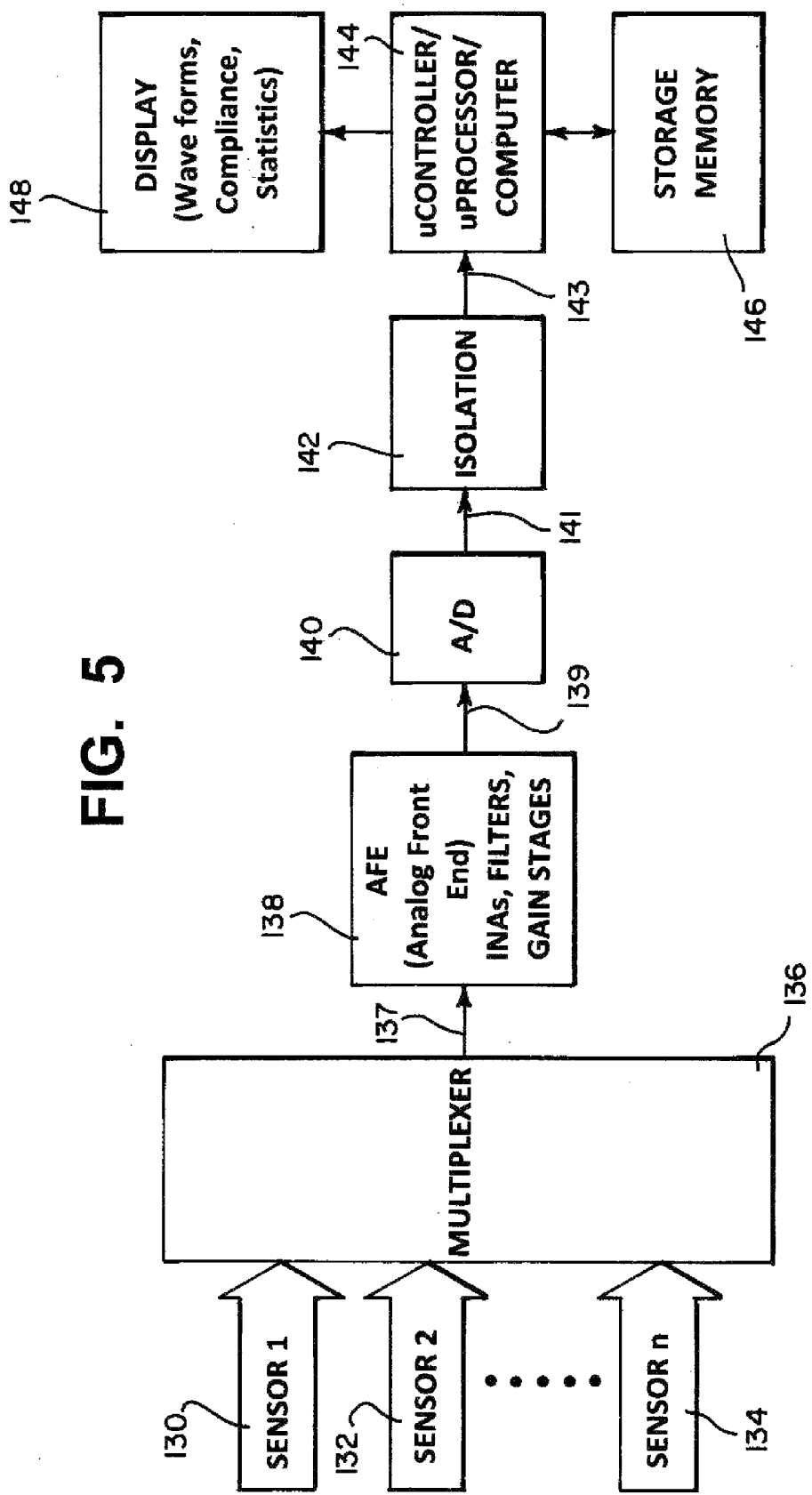
FIG. 5 is a block diagram of one embodiment of a system similar to that shown in FIG. 1B.
Figure 6:
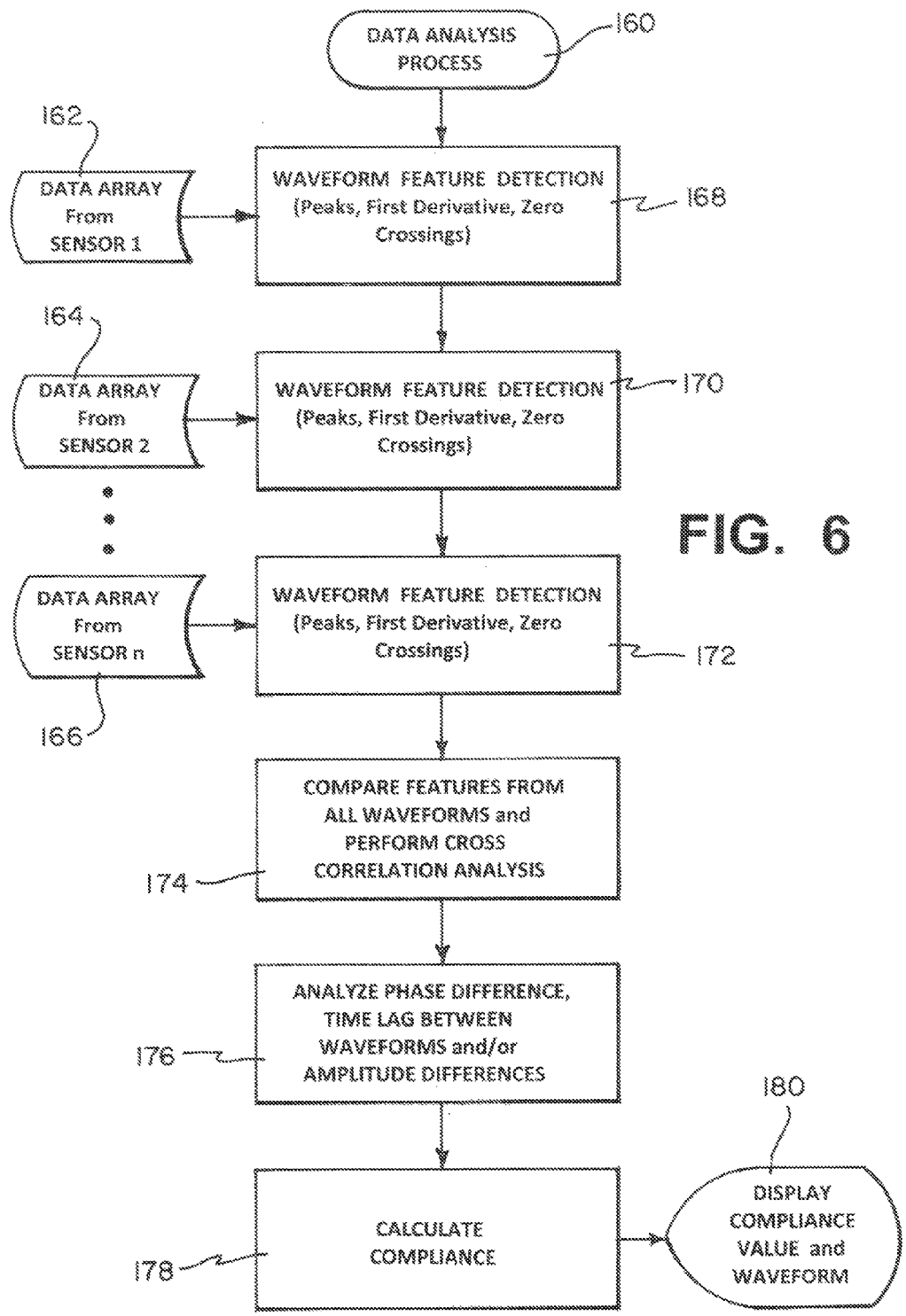
FIG. 6 is a flow chart illustrating signal processing of the system shown in FIG. 5.

A preferred construction and operation of system 10a, which is similar to the system 10 illustrated in FIGS. 1A and 1B, is shown in FIGS. 5 and 6. Signal 130 from sensor 1, signal 132 from sensor 2, and preferably up to and including signal 134 from sensor n are provided to multiplexer 136 which supplies a combined, multiplexed signal 137 to analog front end 138 which may include one or more instrumentation amplifiers, filters and/or gain stages as desired to condition the signals. Adjusted analog signal 139 is provided to analog-to-digital converter 140. The digitized signal 141 is passed through isolation element 142 to enhance patient isolation and safety. Isolated digital signal 143 is passed from element 142 to processor 144 such as a micro-controller, a microprocessor or a type of computer. Data is stored in local or remote media such as storage memory 146 and results, such as one or more waveforms, compliance statistics and/or alarm conditions as described above, are displayed on or by display 148.

In an alternative construction of system 10a, separate analog front end components are provided for each input signals 130 through 134, and the individual processed signals are provided in parallel to a single analog-to-digital converter which provides digital signals in series through a single isolation element to the processor 144. In yet another construction, display 148 provides an audio and/or visual alarm indication when cerebral compliance is calculated as deviating beyond pre-determined limits.

The operation of system 10a is illustrated by the flow chart shown in FIG. 6. The data analysis process is initialized, step 160, and data arrays 162, 164 through 166 for sensors, 1, 2 through n are processed in waveform feature detection steps 168, 170 through 172, respectively. One or more features, also referred to as parameters, from data arrays 162, 164 through 166 are compared and a cross correlation analysis is conducted, step 174. Differences such as phase difference, slopes including take-off points, time lag between waveforms, frequency components and/or amplitude differences are analyzed, step 176. Current cerebral compliance is calculated, step 178, as a running average of the correlation between one or more parameters. The relationship between the compliance and the measured parameters can also be computed as a linear function, a polynomial equation or another empirical formula. Preferably, the system recognizes when current cerebral compliance deviates beyond a pre-selected value. The calculated compliance value, such as current compliance or change in compliance, or at least one perceptible indication of an alarm condition, is displayed or generated, step 180.

Thus, while there have been shown, described, and pointed out fundamental novel features of the invention as applied to preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for monitoring cerebral compliance below the dura mater of the meninges surrounding the brain of a patient, comprising:
    placing a first pressure sensor in a first sub-dural location within the brain;
    placing at least a second pressure sensor in a second sub-dural location within the brain which is different from the first location; and
    connecting the first and second pressure sensors to a system which compares at least one parameter from each of the signals derived from the pressure sensors to estimate cerebral compliance for the patient;
    wherein the system detects a change in the difference between the signals to determine a change in cerebral compliance, and generates a perceptible indication when cerebral compliance deviates beyond a pre-selected value.

2. The method of claim 1 wherein comparing by the system includes determining at least one of a phase difference, a change in slope, and an amplitude difference between the signals.

3. The method of claim 1 wherein the first location is within a ventricle of the brain and the second location is within a tissue of the brain parenchyma.

4. The method of claim 1 wherein the first and second locations are in different tissues of brain parenchyma.

5. The method of claim 4 wherein the first location is within white matter of the brain parenchyma and the second location is within gray matter of the brain parenchyma.

6. The method of claim 1 wherein the first and second locations are within different hemispheres of the brain.

7. The method of claim 1 wherein the first and second sensors are provided on separate structures that are independently positionable within the brain.

8. The method of claim 7 further including surgically creating a single access burr hole through the cranium of the patient and wherein the structures are inserted into the brain through the single access burr hole to place the first and second sensors in first and second sub-meningeal locations.

9. The method of claim 1 further including using at least a third pressure sensor, and positioning the third sensor in a brain tissue that is different than the brain tissue at the first and second locations.

10. The method of claim 1 wherein the first and second locations are spaced from each other by greater than two centimeters.

11. The method of claim 1 wherein the first and second locations are spaced from each other by at least three centimeters.

12. The method of claim 1 wherein comparing by the system includes establishing an initial difference between the signals.

13. The method of claim 1 wherein the system generates a reference pressure propagating signal that travels within the brain, without changing intracranial volume, and compares the parameter from each of the derived signals with the reference signal.

14. The method of claim 13 wherein the system generates the reference signal in at least two frequencies which differ from each other.

15. A method for monitoring cerebral compliance below the meninges surrounding the brain of a patient, comprising:
placing a first pressure sensor in a first sub-meningeal location within the brain to generate a first waveform;
placing at least a second pressure sensor in a second sub-meningeal location within the brain which is different from the first location to generate a second waveform; and
connecting the first and second pressure sensors to a system which compares at least one of phase, slope and amplitude of each of the waveforms generated by the pressure sensors to detect a change in cerebral compliance for the patient, and the system further generates a perceptible indication when cerebral compliance deviates beyond a pre-selected value.

16. The method of claim 15 wherein the second pressure sensor is spaced greater than two centimeters from the first pressure sensor.

17. The method of claim 15 further including using at least a third pressure sensor, and positioning the third sensor in a brain tissue that is different than the brain tissue at the first and second locations.

18. A system for monitoring cerebral compliance below the meninges surrounding the brain of a patient, comprising:
at least first and second pressure sensors, the first pressure sensor positionable in a first sub-meningeal location within the brain, and the second pressure sensor positionable in a second sub-meningeal location within the brain which is different from the first location; and
a signal processor for comparing at least one parameter from each of the signals derived from the pressure sensors to estimate cerebral compliance for the patient and for generating a perceptible indication when cerebral compliance deviates beyond a pre-selected value.

19. The system of claim 18 wherein the signal processor is configured to detect a change in the difference between the signals to determine a change in cerebral compliance.

20. The system of claim 18 further including a reference signal generator for producing at least a first reference signal and a transducer for directing the reference signal to travel within the brain, without changing intracranial volume, and wherein the signal processor compares the parameter from each of the derived signals with the reference signal.

21. The system of claim 20 wherein the system generates the reference signal in at least two frequencies which differ from each other.

22. A method for monitoring cerebral compliance below the dura mater of the meninges surrounding the brain of a patient, comprising:
placing at least a first pressure sensor in a first sub-dural location within the brain; and
connecting the first pressure sensor to a system which generates at least first and second reference pressure propagating signals that travel within the brain, the first reference signal having a first frequency and the second reference signal having a second frequency which differs from that of the first frequency, and the system compares at least one parameter relating to the first and second reference signals from signals derived from the pressure sensor to estimate cerebral compliance for the patient.

23. A system for monitoring cerebral compliance below the meninges surrounding the brain of a patient, comprising:
at least a first pressure sensor positionable in a first sub-meningeal location within the brain;
a reference signal generator which produces at least first and second reference pressure propagating signals, the first reference signal having a first frequency and the second reference signal having a second frequency which differs from that of the first frequency;
a transducer for directing the first and second reference signals to travel within the brain; and
a signal processor for comparing at least one parameter relating to the first and second reference signals from signals derived from the pressure sensor to estimate cerebral compliance for the patient and for generating a perceptible indication when cerebral compliance deviates beyond a pre-selected value.

* * * * *